United States Patent
Kusnetz

Patent Number: 5,714,388
Date of Patent: Feb. 3, 1998

[54] APPARATUS AND METHOD FOR DETECTING CHEMILUMINESCENT LIGHT

[75] Inventor: Jacob Kusnetz, New City, N.Y.

[73] Assignee: Bayer Corporation, Tarrytown, N.Y.

[21] Appl. No.: 696,649

[22] Filed: Aug. 14, 1996

[51] Int. Cl.$^6$ .................................................. G01N 21/76
[52] U.S. Cl. ...................... 436/172; 422/52; 422/82.08; 250/361 C
[58] Field of Search ........................ 422/52, 82.05, 422/82.08, 82.09; 436/172; 250/361 C, 458.1, 459.1, 366

[56] References Cited

U.S. PATENT DOCUMENTS

| | | | |
|---|---|---|---|
| 4,349,510 | 9/1982 | Kolehmainen et al. | 422/52 |
| 4,350,890 | 9/1982 | Geelhood et al. | 422/52 |
| 4,563,331 | 1/1986 | Lossee et al. | 422/52 |
| 4,755,055 | 7/1988 | Johnson et al. | 422/52 |
| 5,260,029 | 11/1993 | Hosoi et al. | 422/82.08 |
| 5,268,147 | 12/1993 | Zabetakis et al. | 422/82 |
| 5,304,492 | 4/1994 | Klinkhammer | 422/82.08 |
| 5,447,687 | 9/1995 | Lewis et al. | 422/52 |
| 5,484,571 | 1/1996 | Pentoney, Jr. et al. | 422/82.08 |
| 5,489,536 | 2/1996 | Ekechukwu | 422/82.08 |

Primary Examiner—Jeffrey Snay
Attorney, Agent, or Firm—Rodman & Rodman

[57] ABSTRACT

The apparatus for detecting chemiluminescent light is a component of a luminometer that can be incorporated in a sample analysis system. Such apparatus, also referred to as a fiber optic read-head, includes a fiber optic cable having a light-transmission end that connects to a photon counter of the luminometer. An opposite end portion of the fiber optic cable is divided into a plurality of fiber optic ribbons. Each of the fiber optic ribbons has a light-receiving end. The ribbons are radially arranged such that the light-receiving ends define a cylindrical passageway for accommodation of a sample analysis tube or cuvette. The fiber optic ribbons are maintained in their desired position by a core. The core is housed in an opaque housing that prevents light from coming in or straying out. Thus, any chemiluminescent light emitted from a tube within the core is collected by the light receiving ends of the fiber optic ribbon and transmitted to the light-transmitting end of the fiber optic cable for conversion into electronic data. The read-head can also be used with input light beams that produce fluorescent light, multi-angled light scattering, polarized light and light of predetermined intensity.

33 Claims, 9 Drawing Sheets

APPARATUS AND METHOD FOR DETECTING CHEMILUMINESCENT LIGHT

BACKGROUND OF THE INVENTION

This invention relates to the detection of chemiluminescence, and more particularly to an apparatus and method for detecting and measuring chemiluminescence in connection with an analyte under test in a sample analysis system.

Sample analysis systems that automatically analyze body fluids such as blood have been developed with the capability of performing multiple analytical tasks in assembly line fashion as detailed in U.S. Pat. Nos. 5,268,147 and 5,399,497. Such analysis systems can carry out multiple high speed immunoassays by providing a stream of sample test packets that flow in a small diameter fluid conduit or analytical line.

Each sample test packet generally includes a series of small liquid volumes or liquid segments separated by air gaps. One or more segments of a sample test packet can contain the analyte to be measured as well as process ingredients such as reagents, buffers for controlling pH levels, and wash material for preventing cross-contamination within the fluid line.

In one known sample analysis system, a sample test packet includes a patient's blood serum as the analyte. The test packet is divided into seven liquid segments by air gaps at the front and rear of each segment in the manner described in U.S. Pat. No. 4,121,466. A preferred chemistry protocol requires that one segment out of every sample test packet of seven segments be the primary focus of analyte measurement. Other segments which may also contain analyte are of secondary interest for purposes of analyte measurement.

Because the analyte is often available in only trace quantities in the body, an accurate means for automatically measuring the presence and quantity of such analyte is needed.

It is known that the combination of an analyte with a reagent to form a predetermined chemical reaction can facilitate detection and quantification of the analyte. Since some chemical reactions are also known to produce light at extremely low levels of analyte, chemiluminescence has been recognized as a potential vehicle for detecting and quantifying an analyte under test. However, apparatus for detecting chemiluminescence in the environment of a sample analysis system of the type referred to must be of a design and size that is operable without interfering with the sample tests that are being conducted.

It is thus desirable to provide an efficient apparatus for collecting light from small liquid segments for measuring the presence and quantity of a minute amount of analyte in a liquid segment of a multi-segment test packet. It is also desirable that the detection apparatus for collecting and transmitting chemiluminescence be robust, easily serviced, operate without the need for precise settings and not interfere with the processing of test packets in a sample analysis system.

OBJECTS AND SUMMARY OF THE INVENTION

Among the several objects of the invention may be noted the provision of a novel apparatus for collecting and transmitting chemiluminescence, a novel apparatus for collecting and transmitting chemiluminescence which can be positioned around a fluid flow tube containing analyte, a novel apparatus for collecting and transmitting chemiluminescence which can receive a cuvette containing analyte, a novel apparatus for collecting and transmitting chemiluminescence which accommodates a fluid flow tube or a cuvette, a novel apparatus for collecting and transmitting chemiluminescence which is operable without moving parts, a novel apparatus for collecting and transmitting chemiluminescence which is capable of providing quantitative measurements at relatively high speed, a novel apparatus for collecting and transmitting chemiluminescence which does not require adjustment and is not subject to alignment problems, a novel apparatus for collecting and transmitting chemiluminescence which efficiently detects and measures chemiluminescence, a novel luminometer, and a novel method of detecting chemiluminescence.

Other objects and features of the invention will be in part apparent and in part pointed out hereinafter.

In accordance with the invention, a read-head for a luminometer employs a fiber optic cable. The fiber optic cable includes a light-transmission end that releasably connects to a photon counter of the luminometer. An opposite end portion of the fiber optic cable is divided into a plurality of fiber optic ribbons.

The fiber optic ribbons are radially arranged within an opaque housing of the read-head, such that the free ends of the fiber optic ribbons are centrally directed within a cylindrical core. The free ends of the fiber optic ribbons, which are also the light-receiving ends of the fiber optic cable, thus define a cylindrical passageway at the center of the core that accommodates an analytical tube of a sample analysis system or a cuvette. In instances where analyte is disposed in an analytical tube, the analytical tube also passes through a bubble detector that detects air bubbles. Air bubble detection is employed in the luminometer to synchronize operation of the read-head, in combination with the analytical tube. Air bubble detection is not needed in instances where analyte is disposed in a cuvette.

The cylindrical core of the read-head is preferably constituted by individual segments that resemble cut sections of a pie. A respective fiber optic ribbon is sandwiched between two neighboring cylindrical segments. The cylindrical segments maintain each of the fiber optic ribbons in a band-like form, wherein the band is generally rectangular in cross-section and extends a predetermined lateral distance along the axis of the analytical tube.

The cylindrical core and the radial arrangement of fiber optic ribbons are maintained in a fixed position within the housing. The housing forms a light-proof enclosure for the core and any portion of the fiber optic ribbons and cable that are located within the housing. Aligned openings in opposite front and rear walls of the housing also align with the cylindrical passageway defined by the light-receiving ends of the fiber optic ribbons. The analytical tube can thus extend through the read-head housing in the cylindrical passageway.

Under this arrangement, the read-head does not require any adjustment, since it receives the analytical tube at a predetermined central passage in the core. The read-head is a non-invasive, non-interfering, analyte detection component for a sample analysis system that provides circumferential collection of chemiluminescence from an analytical tube of the sample analysis system.

In a further embodiment of the invention, the rear wall of the read-head has no opening and the read-head is oriented such that the rear wall is horizontal. The read-head is thus adapted to receive cuvettes rather than an analytical tube.

In another embodiment of the invention, a reflecting mirror replaces several fiber optic ribbons such that some chemiluminescent light is reflected from the mirror back through the analytical tube into the light-receiving ends of the remaining fiber optic ribbons disposed around a peripheral portion of the analytical tube.

The invention also includes a method for collecting and transmitting light. The method includes arranging a plurality of fiber optic ribbons radially around an axis such that corresponding light-receiving end portions of the fiber optic ribbons are substantially equidistant from the axis and define a cylindrical passageway around the axis. The method further includes collecting any chemiluminescent light established within the cylindrical passageway through the light-receiving ends of the fiber optic ribbons. The method also includes transmitting light from the light-receiving ends of the fiber optic ribbons to a receiving station for conversion of the light into selected data. The light collection can be randomized or coherent. Furthermore, the light transmission can be randomized or coherent.

The invention accordingly comprises the constructions and method hereinafter described, the scope of the invention being indicated in the claims.

DESCRIPTION OF THE DRAWINGS

In the accompanying drawings.

Corresponding reference characters indicate corresponding parts throughout the several views of the drawings.

DETAILED DESCRIPTION OF THE INVENTION

As used herein, the term "tube" is intended to refer to cuvettes and analytical lines or analytical tubes.

Figure 1:
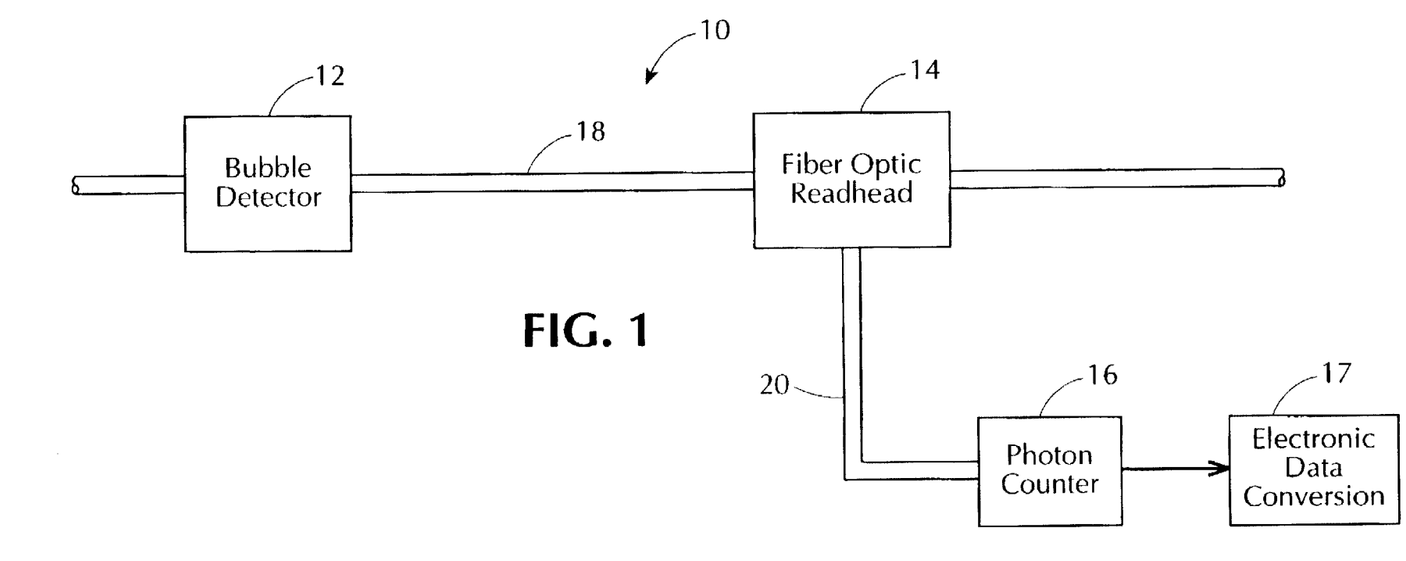
FIG. 1 is simplified schematic block diagram of a luminometer incorporating the present invention.

Referring to the drawings, a luminometer system 10 incorporating one embodiment of the invention, is shown in simplified block diagram in FIG. 1.

The luminometer 10 includes a bubble detector 12, a fiber optic read-head 14, also referred to as an apparatus for collecting and transmitting chemiluminescence, and a photon counter 16. Electronic data conversion components that follow the photon counter 16 are generally indicated by the reference number 17. An analytical line 18, which receives fluid sample being tested, extends through the bubble detector 12 and the fiber optic read-head 14. The analytical line 18 is a transparent plastic tube, preferably formed of Teflon® material. A fiber optic cable 20 extends from the read-head 14 to the photon counter 16, and may also extend to other components (not shown) of a sample analysis system.

Figures 3, 7:
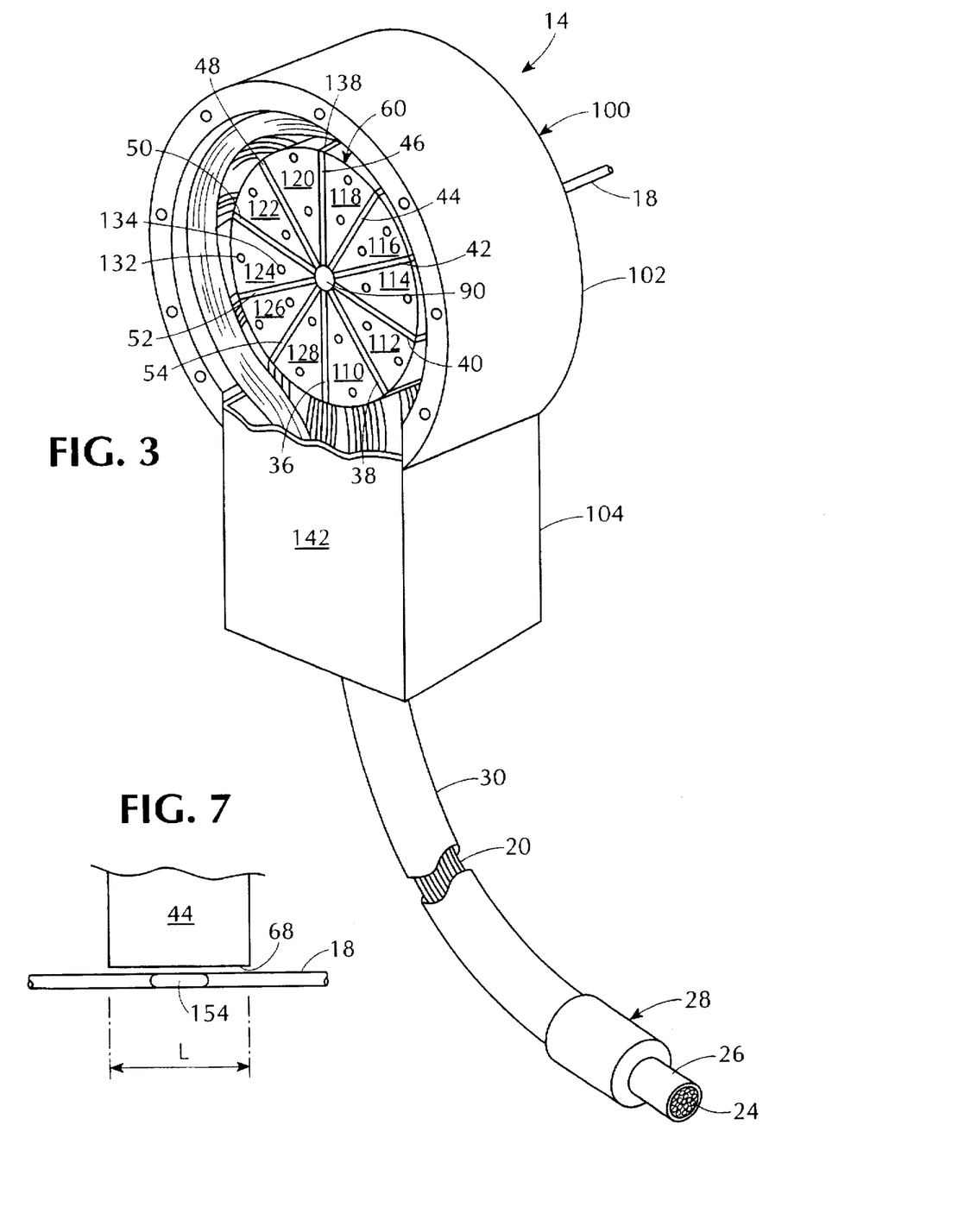
FIG. 3 is a perspective view of a fiber optic read-head employed in the luminometer.
FIG. 7 is a fragmentary profile view of an optic fiber ribbon proximate the analytical tube.
Figure 8:
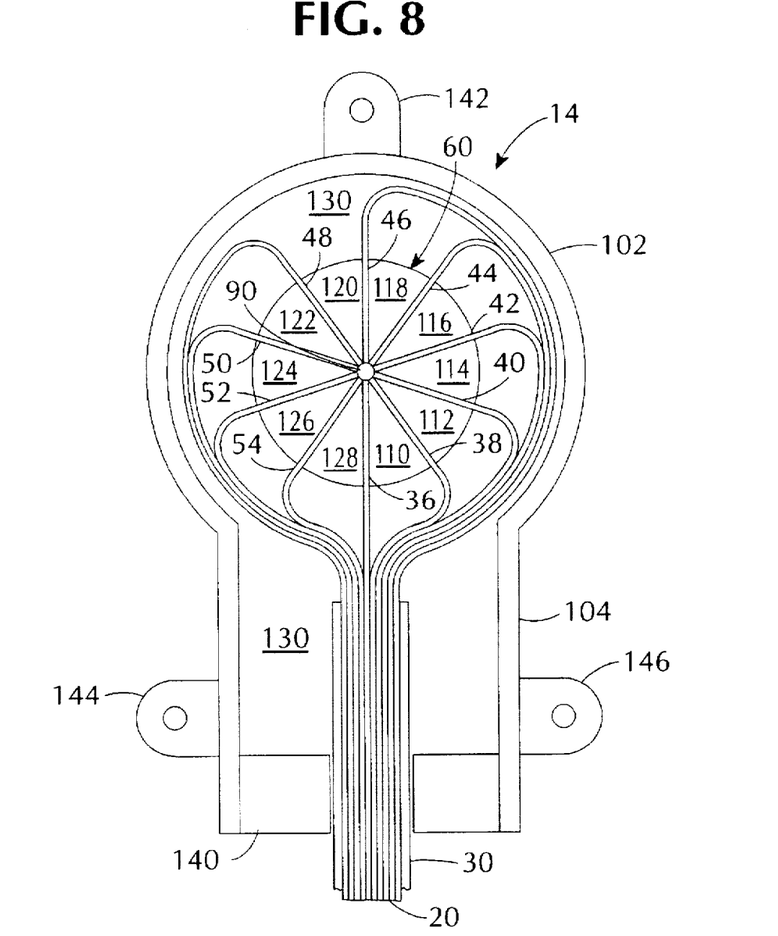
FIG. 8 is a simplified plan view of the read-head of FIG. 3.

Referring to FIGS. 3 and 8, the fiber optic cable 20 has a light transmission end 24 secured within a reduced neck portion 26 of a connector 28 that is engageable with the photon counter 16 in any suitable known manner. The fiber optic cable 20, which is surrounded by an opaque protective sheath 30, is divided into ten fiber optic ribbons 36–54, as most clearly shown in FIG. 8. It should be noted that the number of fiber optic ribbons used is a matter of choice depending on system requirements for light detection.

The fiber optic ribbons 36–54 are supported in radial arrangement in a cylindrical core 60 such that free ends 66, 68, 70, 72, 74, 76, 78, 80, 82 and 84 (FIG. 5) of the respective fiber optic ribbons 36–54 define a generally cylindrical passageway 90. The cylindrical passageway 90 is approximately 3.4 millimeters diameter to accommodate the analytical tube 18, which has an outer diameter of approximately 2.85 millimeters and an inner diameter of approximately 2.2 millimeters.

The free ends 66–84 of the fiber optic ribbons 36–54 function as light-receiving ends of the fiber optic cable 20. Under this arrangement, the radial clearance in the read-head 14 between the analytical line 18 and the light-receiving ends of the fiber optic ribbons is approximately 0.275 millimeters.

Figure 2:
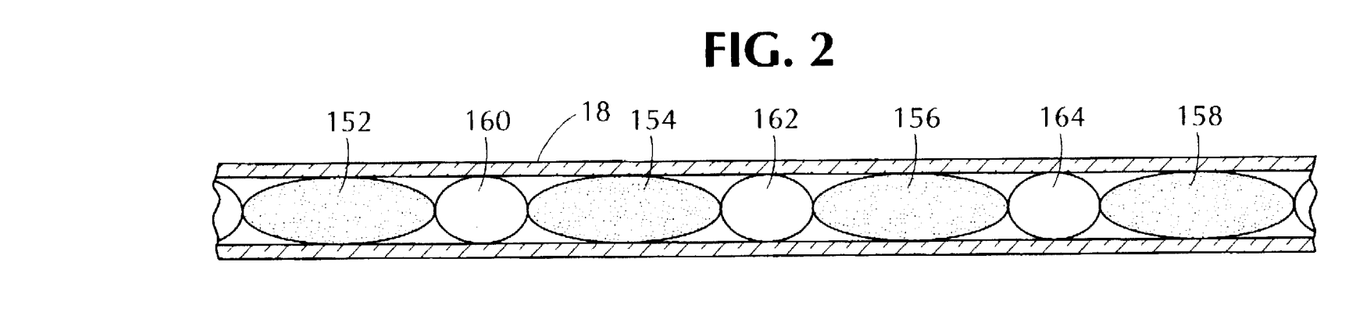
FIG. 2 is an enlarged fragmentary sectional view of an analytical tube containing segments of a test packet that are subject to luminometer examination.
Figures 4, 5, 6:
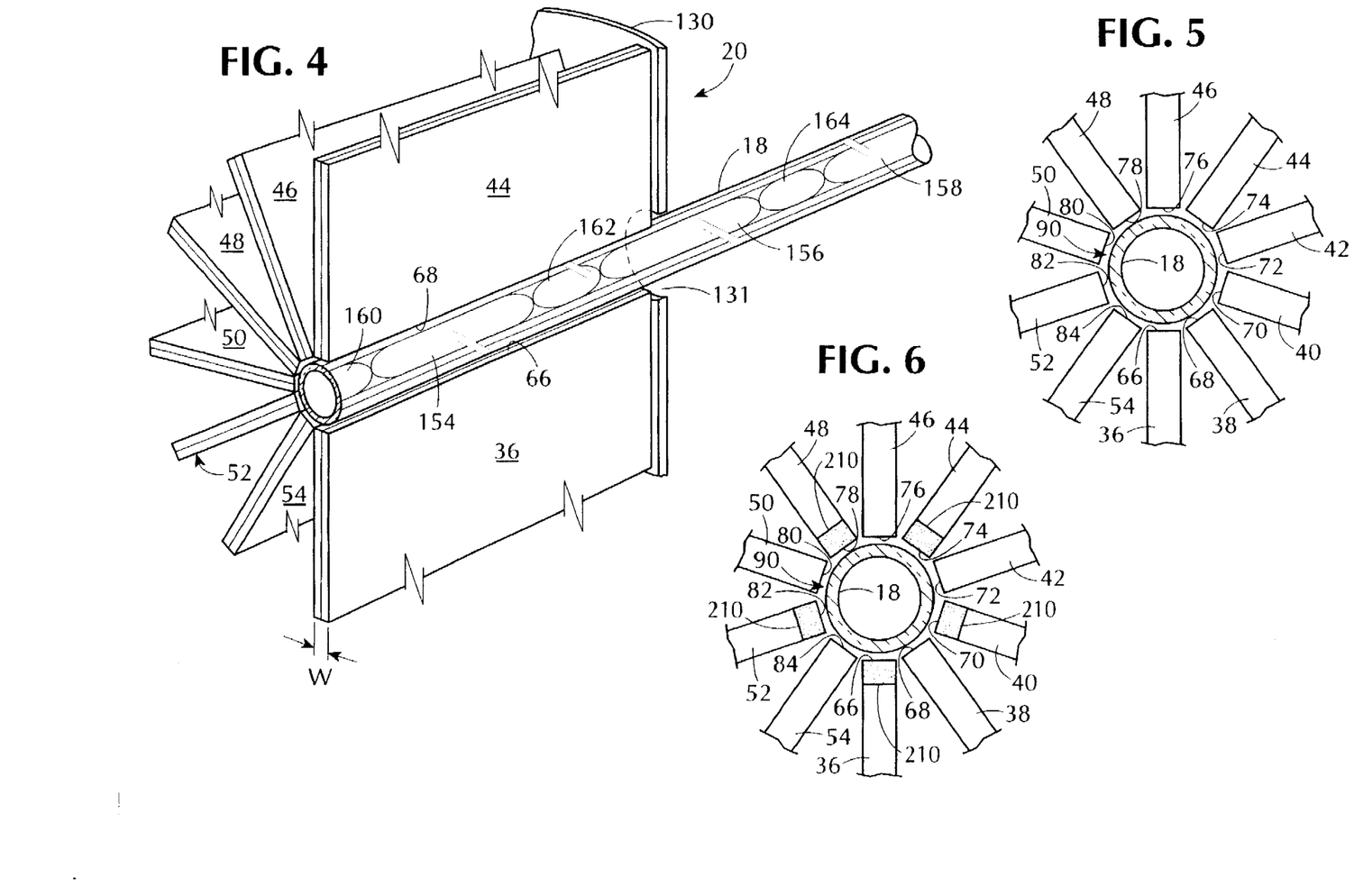
FIG. 4 is an enlarged fragmentary perspective view of fiber optic ribbons from the read-head that surround the analytical tube.
FIG. 5 is a fragmentary end view thereof.
FIG. 6 is a view similar to FIG. 5 with polarizing material provided at some of the light-receiving ends of the fiber optic ribbons.

Preferably, the end face of light-receiving ends 66–84 is generally rectangular, as most clearly shown by the light-receiving end 66 of the fiber optic ribbon 36 in FIG. 4. The light-receiving ends 66–84 thus extend a predetermined axial length L (FIG. 7) of approximately 15 millimeters along the analytical line 18, and have a predetermined width W (FIG. 4) of approximately 1 millimeter. Liquid segments such as 152, 154, 156 and 158 (FIGS. 2 and 4) in the analytical line 18 are generally approximately 7.4 millimeters long. Air segments or air bubbles such as 160, 162 and 164, which separate the liquid segments, are generally approximately 4.2 millimeters long.

The core 60 maintains the fiber optic ribbons 36–54 in a band having a rectangular cross-section, as most clearly shown in FIG. 4. The core 60 also maintains the radial positioning of the fiber optic ribbons 36–54 such that the light-receiving end portions 66–84 are in a fixed position to define the cylindrical passageway 90. Bonding material (not shown) can also be provided at the band portions of the fiber optic ribbons 36–54 to maintain the desired rectangular form of the bands.

The core 60 is supported within a light-proof opaque housing 100 of the read-head 14. The housing 100 includes a cylindrical shell portion 102 and a rectangular neck portion 104, which can be formed integrally. The core 60 can be formed as a one-piece structure, but is preferably constituted of ten individual segments 110, 112, 114, 116, 118, 120, 122, 124, 126 and 128. The segments 110-128 are individually secured to a back wall 130 (FIG. 8) of the cylindrical shell 102 by bonding or by fasteners (not shown) that engage the fastener holes 132 and 134 (FIG. 3) in each segment.

The segments 110-128 are preferably plastic, opaque material and, as positioned, define ten radial slots 138 (FIG. 3) that accommodate the respective fiber optic ribbons 36-54. A collar portion 140 (FIG. 8) within the neck portion 104 accommodates the sheathed fiber optic cable 20. Any suitable known light-proof seal is provided between the cable sheath 30 and the collar 140.

A front cover 142 (FIG. 3) secures to the front portion of the cylindrical shell 102 and the neck 104 and includes a central opening (not shown) with respect to the shell 102 that aligns with the cylindrical passageway 90 of the core 60, and also aligns with a corresponding central opening 131 (FIG. 4) in the back wall 130.

Each of the fiber optic ribbons 36-54 is formed of a predetermined number of optic fibers, preferably formed of plastic, and having a diameter of approximately 0.5 millimeters and a numerical aperture (NA) of 0.5 (acceptance angle of +/-30°). The fiber diameter and plastic material are chosen primarily for durability, ease of handling and assembly, especially since plastic fibers do not break as easily as glass. Other properties of plastic fibers, such as spectral transmission and possible fluorescence, are not considered detrimental since the fiber ribbons are intended for use in the visible spectral region where they have high transmission and are not exposed to ultraviolet light. Approximately sixty optic fibers having a packing fraction of 78% are used in each of the fiber optic ribbons 90-108.

It should be noted that the size of the cylindrical shell 102 is dependent upon the allowable bend radius of the fibers in the fiber optic ribbons. As presently contemplated, the fiber optic ribbons 36-54 can be accommodated in a cylindrical housing shell 102 approximately three inches in diameter.

The read-out housing 100 is mounted inside a temperature controlled chamber (not shown) of an analysis system with the fiber optic cable 20 leading to a photomultiplier tube assembly of the photon counter 16. This arrangement permits flexibility in instrument packaging and enhances serviceability. Attachment ears such as 142, 144 and 146 can be provided on the cylindrical shell 102 and the neck 104 to facilitate securement of the read out head 14 to any desired location within an analytical system.

In using the fiber optic read-head 14, the analytical line 18 is threaded through the opening (not shown) in the front cover 142 of the cylindrical shell 102, the cylindrical passageway 90 at the center of the core 60, and the corresponding aligned opening 131 (FIG. 4) in the back wall 130 of the cylindrical shell 102. The analytical line 18 thus conveys an air segmented liquid stream of test packets through the fiber optic read-head 14. The read-head 14 senses chemiluminescence as a method for detecting and quantifying an analyte under test.

Ideally for maximum light collection, each light-transmitting end portion 66-84 of the fiber optic ribbon should be tangent to its neighbor without any gap between. However, under the dimensional arrangement previously described, a gap of about 0.050 to 0.080 millimeters between the end portions 66-84 is obtained.

As previously noted, one of the liquid segments, such as 152, 154, 156 and 158, out of every group of seven segments in a test packet contains the chemiluminescent reaction to be measured. A combination of heat treatment and the thin wall structure of the analytical tube 18 render the analytical tube 18 transparent to a wide wave length range which includes the wave lengths of light emitted by the chemiluminescent reaction. For example, wave lengths of 500 NM are detectable in accordance with the invention described herein.

In using the luminometer 10 which incorporates the read-head 14, the bubble detector 12, which is of known construction and operation, senses the air bubble interface such as 160, 162 and 164 between the liquid segments such as 152, 154, 156 and 158 in the analytical line 18. The bubble detector 12 provides a signal that is used to track the stream of test packets in the analytical line 18 by detecting the air bubbles. Air bubble detection is used to synchronize the operation of the read-head 14 and monitor and control the data acquisition cycle. The bubble detector 12 also senses the direction of the stream flow, which can be in a forward or reverse direction.

Chemiluminescent light emitted by the reaction between analyte and reagent in a selected analyte segment monitored by the bubble detector 12 is collected at the light-receiving end portions 66-84 of the fiber optic ribbons 36-54. The collected light is transmitted through the fiber optic cable 20 to the transmission end 24, which connects to the photon counter 16. The photon counter 16 is a known component, and includes a known photomultiplier tube. The photon counter 16 converts the chemiluminescent light signals to electronic signals that are identified and operated on by system electronics indicated at reference number 17 in FIG. 1, and correlated with known criteria for identifying and quantifying analytes. Electronic data collection and conversion do not form a part of this invention.

Figure 9:
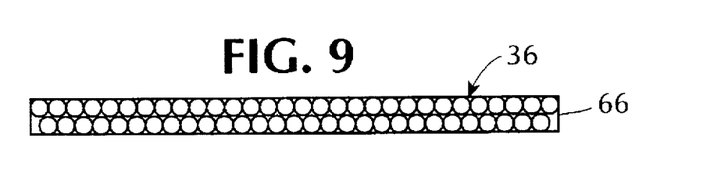
FIG. 9 is a simplified schematic end view of the light-receiving end of a fiber optic ribbon with optic fibers in nested orientation.
Figure 10:
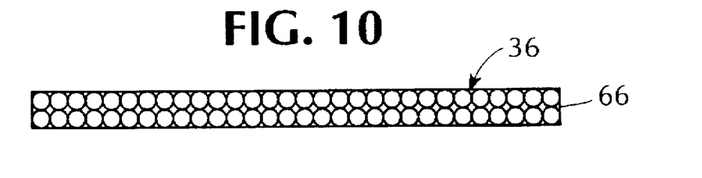
FIG. 10 is a view similar to FIG. 9 with optic fibers in aligned orientation.

The optic fibers in each of the fiber optic ribbons 36-54 can be in a nested arrangement, such as shown by the light-receiving end 66 of the fiber optic ribbon 36 in FIG. 9, or an aligned arrangement, such as shown for the same fiber optic ribbon 36 in FIG. 10. In the aligned arrangement, the optic fibers can be spatially ordered both at the light-receiving ends 66-84 and at the light-transmission end 24 to form a coherent arrangement.

Figure 11:
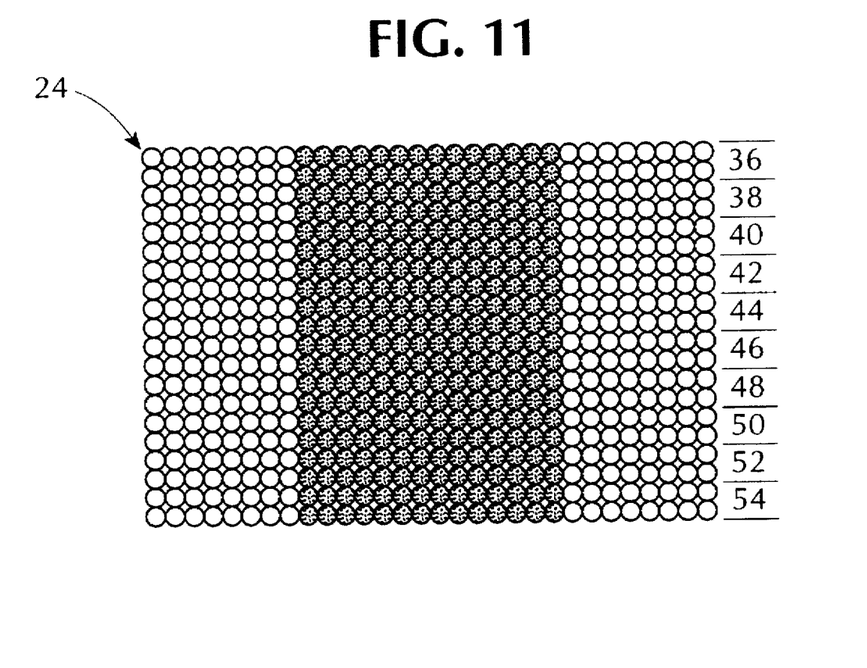
FIG. 11 is a coherent light-transmission pattern at the light-transmission end of a fiber optic cable.
Figure 12:
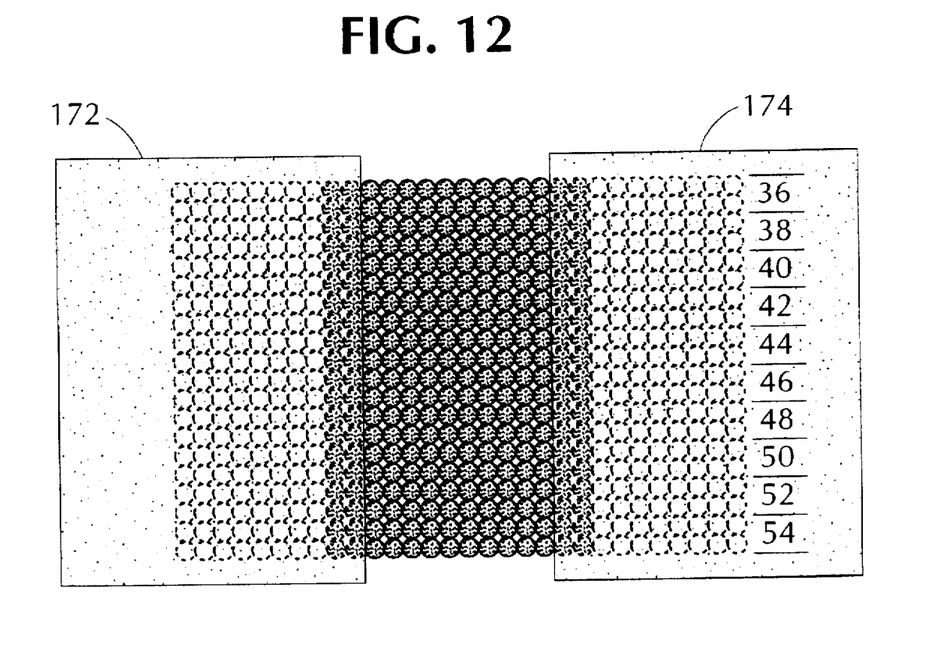
FIG. 12 shows a masking of the pattern of FIG. 11.

In the coherent arrangement, the light-transmission end 24 is rectangular rather than circular, such as shown in FIG. 11. The rectangular dimensions of the light-transmission end 24 are approximately 10 by 15 millimeters based on a layering of the light-transmission ends of each of the ten fiber optic ribbons 36-54. The light-transmission end of each fiber optic ribbon 36-54 is approximately 1 millimeter by 15 millimeters. Under this arrangement, the light-transmission end 24 represents a 1:1 image of the analytical line and the segmented stream, such as shown in FIG. 11. Each optic fiber represents one pixel of that image. The pixels can be selectively blocked by masks 172 and 174, such as shown in FIG. 12, to change the light collection features of the read-head 14. Thus, blocking can be used to change the view volume, or eliminate stray light.

For either the nested or aligned arrangements of FIGS. 9 or 10, the optic fibers can be spatially randomized at the light-transmission end. There is no 1:1 spatial correspondence of fibers, and no image is formed. This randomized arrangement has the advantage of reducing the effect of any variations of sensitivity of the photomultiplier tube detector surface and thus gives a more complete integration of the light signal.

The randomized arrangement of fibers is less expensive to manufacture than the coherent arrangement, and allows the output light-transmission end 24 (FIG. 3) of the cable 20 to be circular in shape for a more compatible match with the photomultiplier tube and photon detector 16. Thus, the randomized arrangement is the preferred arrangement for the read-head 14.

Figure 13:
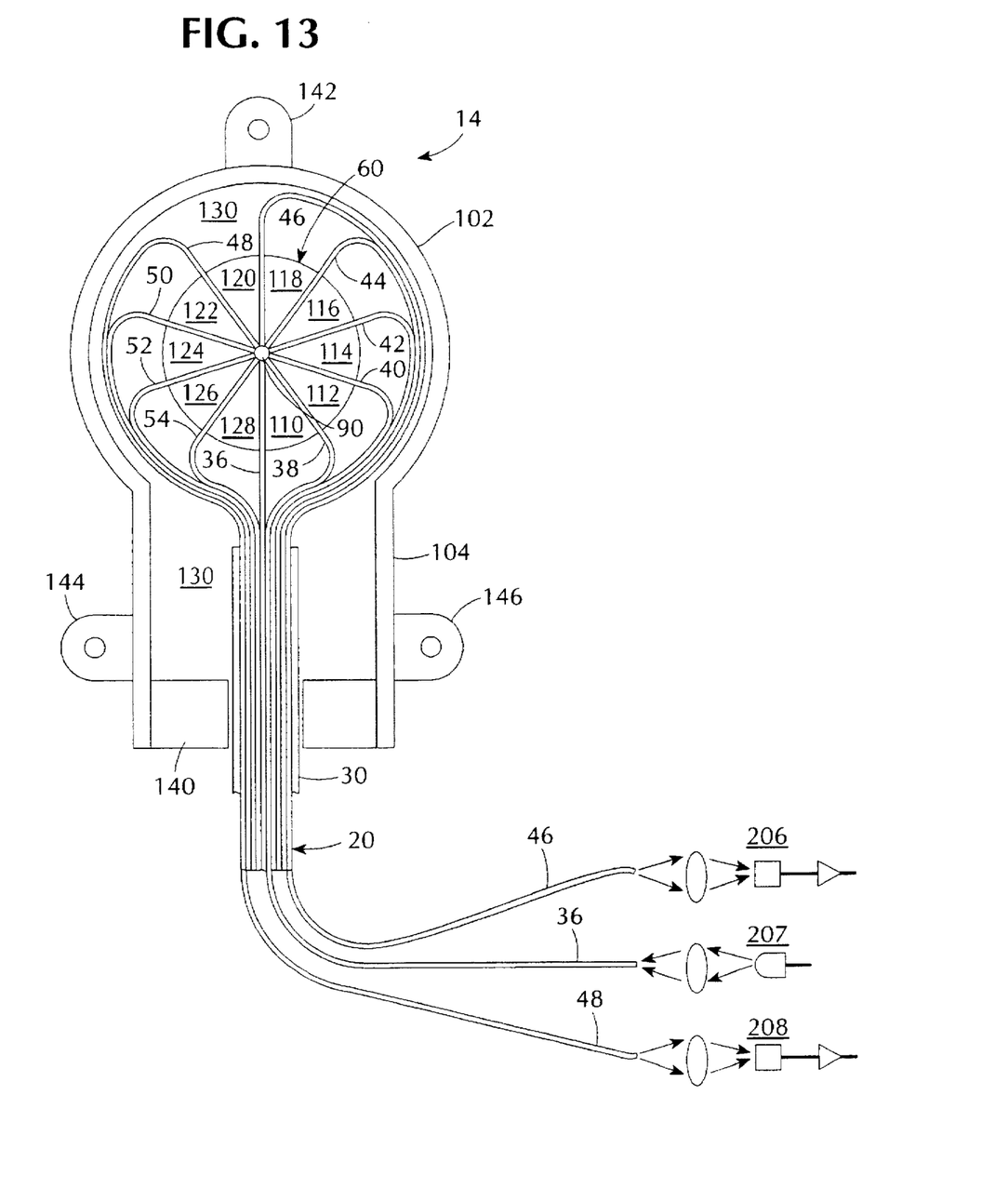
FIG. 13 is a plan view of another embodiment of the invention.

The read-head 14 can be configured for other measurement modalities, such as fluorescence, multi-angle light scattering, light absorption, and polarization (fluorescence or scattering) methods. These applications can be accomplished by bringing the fiber optic ribbons out of the cylindrical shell 102 as separate cables 36, 46 and 48, such as shown in FIG. 13. Under the FIG. 13 arrangement, any or all of the fiber optic ribbons can be used as separate cables for selected illumination or detection functions, as desired, and as indicated schematically at reference numbers 206, 207 and 208.

Figures 14, 15:
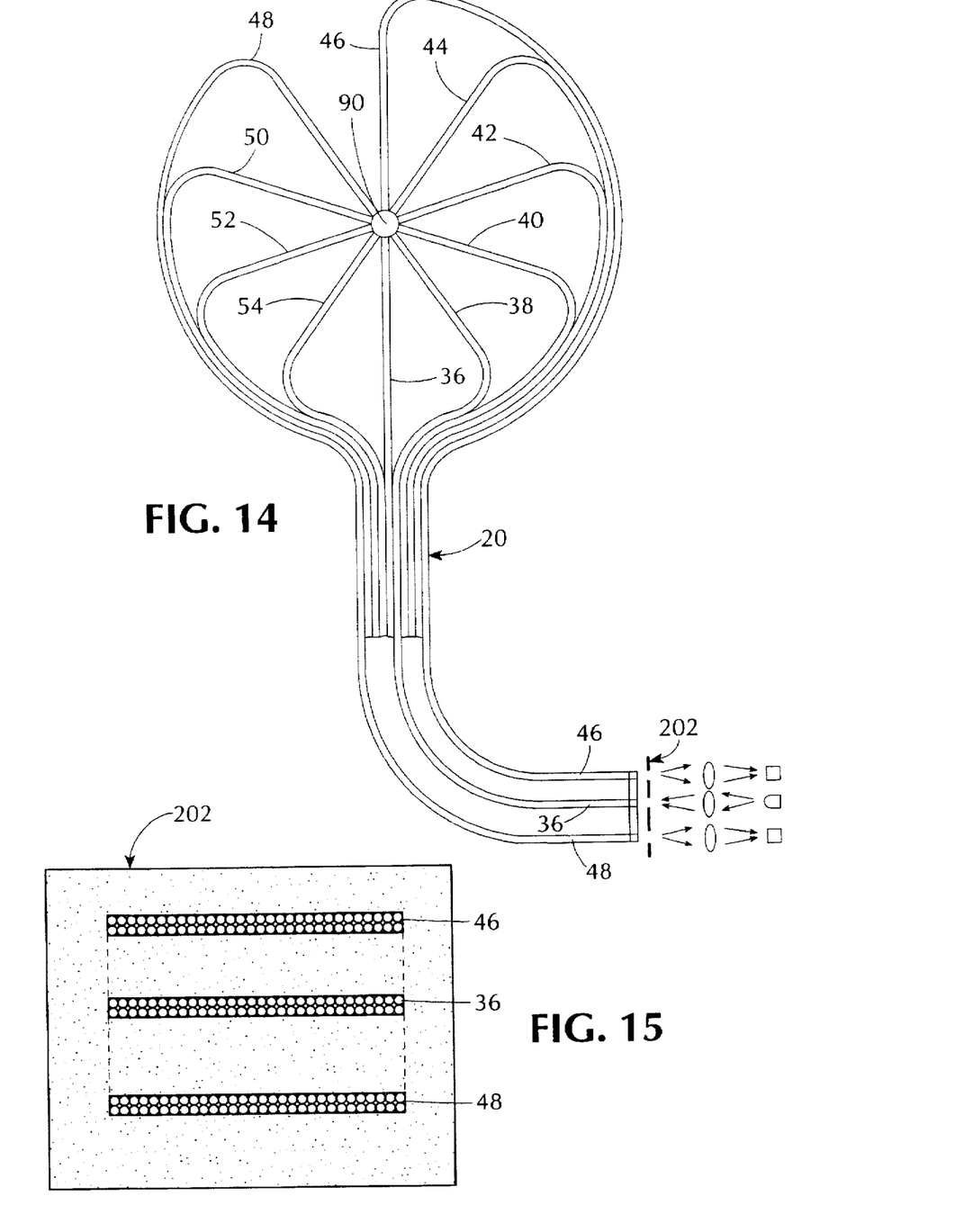
FIG. 14 is a plan view of the fiber optic ribbons of FIG. 13.
FIG. 15 is a masked coherent light-transmission pattern for the embodiment of FIG. 13.

As a further option, with reference to FIG. 14, the coherent arrangement of fiber optic ribbons 36–54 can be brought out of the housing 100 as a single cable. A mask 202 (FIG. 15) can be placed over the output end of the single cable to select individual ribbons for illumination or detection, as shown in FIG. 15.

If desired, several masks representing several measurement modalities can be placed on a wheel (not shown) and indexed into place as required by a particular application. For polarization applications, a thin polarizer plate (not shown), which is generally available as plastic polarizing sheet 210 (FIG. 6), can be placed over the light-receiving ends 66, 70, 74, 78 and 82 of selected fiber optic ribbons 36, 40, 44, 48 and 52, or between the analytical line 18 and the light-transmission ends. In general, the fiber optic ribbons would not preserve the state of polarization as light is transmitted from the light-receiving end to the light-transmission end.

Figure 16:
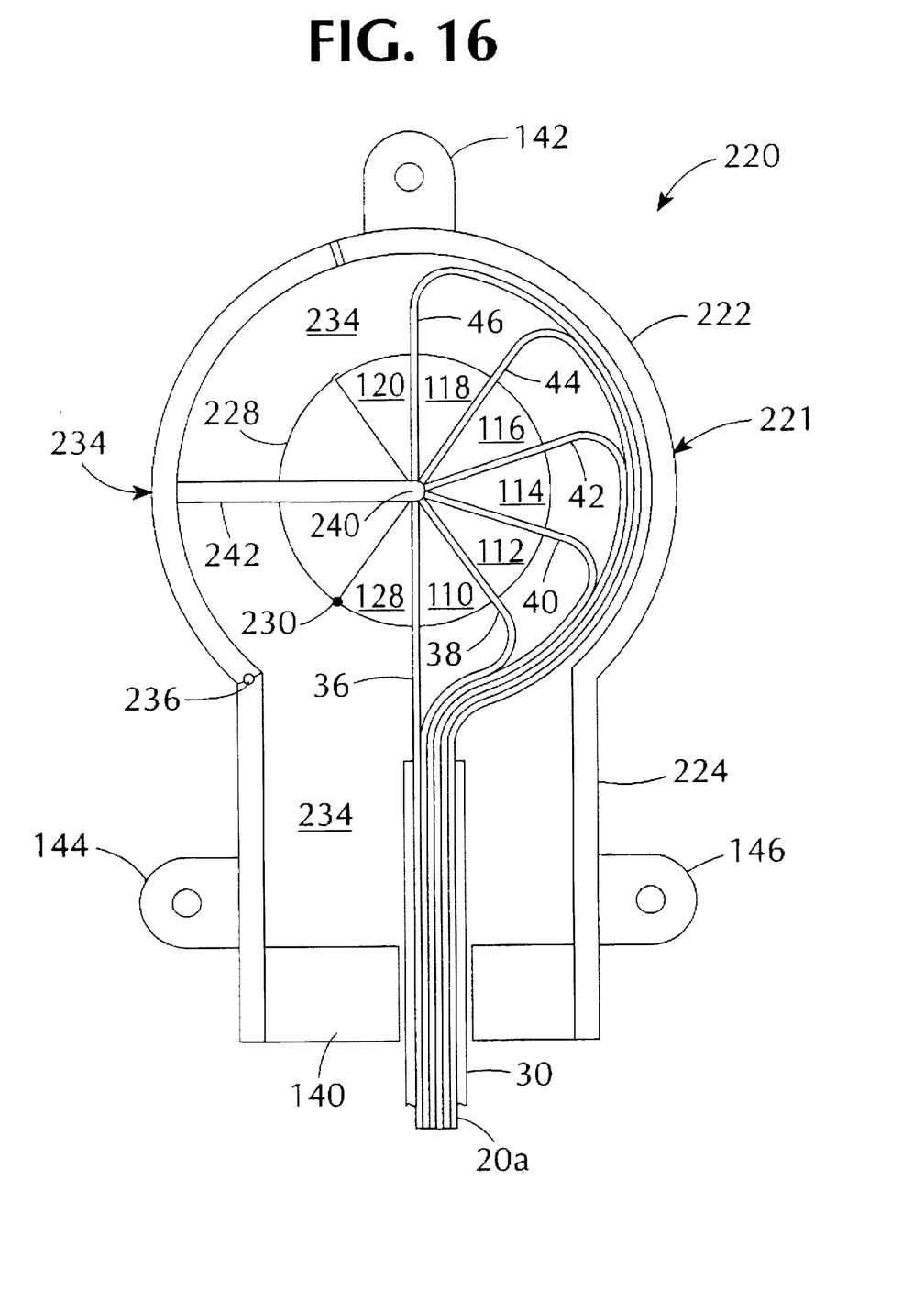
FIG. 16 is a further embodiment of the invention.

Another embodiment of the fiber optic read-head is generally indicated by the reference number 220 in FIG. 16. The read-head 220 includes a housing 221 with a cylindrical shell 222 and a neck 224 corresponding to the shell 102 and the neck 104 of the read-head 14. The read-head 220 differs from the read-head 14 by elimination of the fiber optic ribbons 48, 50, 52 and 54 and the segments 124 and 126. The eliminated elements are replaced with a concave mirror 228 that is pivoted at 230 to the segment 128.

The mirror 228 is in a reflecting position when it aligns with or bears against the segment 120. A door section 234 of the housing shell 222 is pivotable at 236 to an open position and the mirror 228 is likewise pivoted away from the segment 120 to permit placement of the analytical line 18 directly into a passageway 240 defined by the light-receiving ends 66, 68, 70, 72, 74 and 76 of the fiber optic ribbons 36–46.

Once the analytical line 18 is positioned in the passageway 240, the mirror 228 and the door 234 of the housing shell 222 can be closed. The read-head 220 is rendered light-proof in any suitable known manner. It should be noted that the back wall 234 of the housing 221 is provided with an open-ended slot 242 to accommodate disposition of the analytical line 18 into the central passage 240 when the door 234 and the mirror 228 are opened. A similar aligned slot (not shown) is provided in a front cover (not shown) of the housing 221. The slots are masked or suitably covered to prevent light leakage once the analytical line 18 is positioned in the read-head 220.

In using the fiber optic read-head 220, the analytical line 18 is positioned in the passage 240. Light emitted from the analytical line 18 by a chemiluminescent segment containing analyte is transmitted to the light-receiving ends 66–76 of the fiber optic ribbons 36–46 by direct flow to the light-receiving ends and also by reflection from the mirror 228.

The mirror 228 reflects chemiluminescent light from the analytical line 18 in the passageway 240 back toward the axis of the analytical line 18 for transmission into the light-receiving ends 66–76 of the fiber optic ribbons. The received light is transmitted to a light-transmission end (not shown) of the fiber optic cable 20a and converted to electronic data in a manner similar to that previously described for the read-head 14.

The read-head of the present invention is also adaptable for use with a cuvette rather than the analytical line 18.

Figure 17:
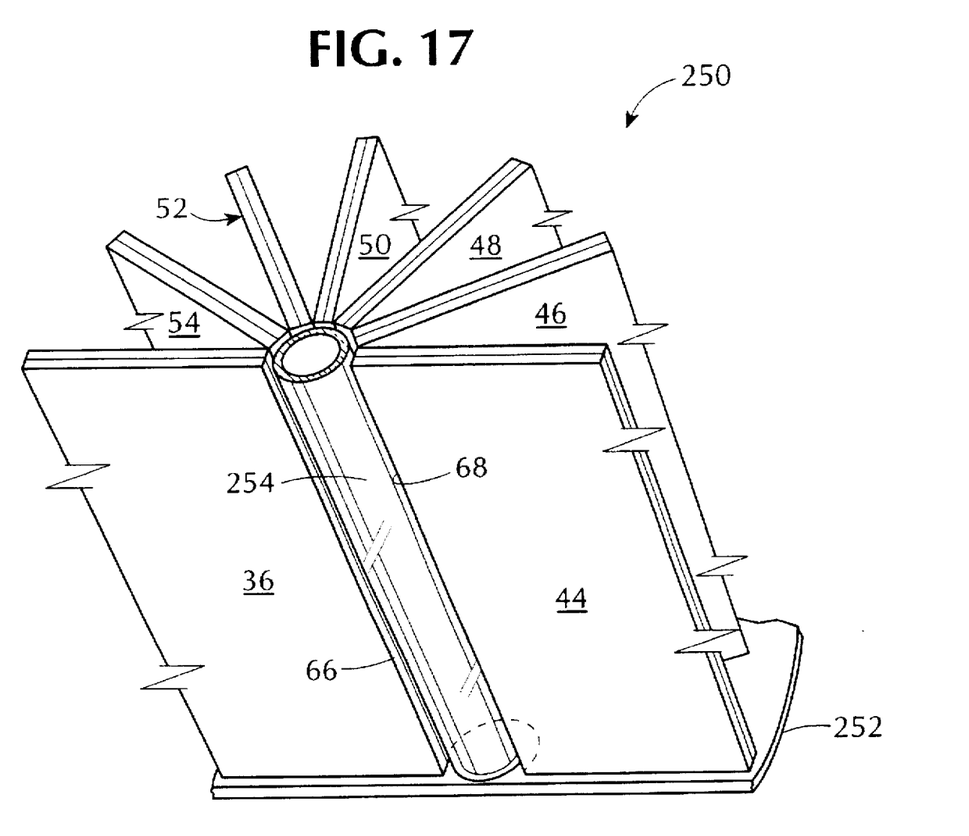
FIG. 17 is an enlarged fragmentary perspective view of fiber optic ribbons from a read-head that receives a cuvette.

Referring to FIG. 17, a read-head 250 includes a back wall 252 that corresponds to the back wall 130 of the read-head 14. However, the back wall 252 does not have any openings. The read-head 250 is otherwise identical to the read-head 14.

The read-head 250 is adapted to receive a cuvette 254 containing analyte for purposes of quantifying the analyte using chemiluminescence or any of the other analyte detection procedures previously described. However, the read-head 250 is used without the bubble detector 22 and is positioned such that the back wall 252 is horizontal.

Thus, the cuvette 254 can be vertically installed in a read-head 250 by disposition in the opening (not shown) in the front wall 142 of the read-head housing, and in the aligned cylindrical passageway 90 (FIG. 5) defined by the light-receiving end portions 66–84 of the fiber optic ribbons 36–54. When the detection operation is completed, the cuvette 254 is removed from the read-head 250 and another cuvette is positioned therein.

Some advantages of the present invention evident from the foregoing description include a fiber optic read-head that embraces a fixed peripheral section of an analytical line or cuvette to receive chemiluminescent light emitted by an analyte in a cuvette or as it moves in a liquid segment through the analytical line. The fiber optic read-head does not require adjustment, can be easily installed into a sample analysis system and permits easy insertion and removal of an analytical line or cuvette. The read-head can be adapted for randomized or coherent light transmission. In addition, the read-head is a portable modular component that is durable and relatively easy to manufacture.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. An apparatus for collecting and transmitting chemiluminescent light comprising
   a) a plurality of fiber optic ribbons,
   b) each said fiber optic ribbon including a predetermined number of optic fibers having opposite ends, one end of each of said optic fibers in said fiber optic ribbons being a light-receiving end, and the opposite end of each of said optic fibers in said fiber optic ribbons being a light-transmission end,
   c) said plurality of fiber optic ribbons being radially arranged around a lateral axis to define a cylindrical passageway wherein said light-receiving ends of said fiber optic ribbons are substantially equidistant from said lateral axis, said cylindrical passageway being sized to receive a tube containing liquid with analyte undergoing chemical reaction such that chemiluminescent light emitted by said chemical reaction can pass through the light-receiving ends of said fiber optic ribbons to corresponding said light-transmission ends, and d) means for collectively maintaining the radial arrangement of said fiber optic ribbons and the positioning of the light-receiving end portions substantially equidistant from said lateral axis in a light proof enclosure.

2. The apparatus as claimed in claim 1, including means for collecting together in the form of a cable the light-transmission ends of said fiber optic ribbons, such that said light-transmission ends are constituted as an end of the cable.

3. The apparatus as claimed in claim 1, wherein the light-transmission ends of said fiber optic ribbons are separate from each other.

4. The apparatus as claimed in claim 1 further including a photon counter cooperable with the light-transmission ends of said fiber optic ribbons to convert chemiluminescent light transmitted through said fiber optic ribbons into electronic signals.

5. The apparatus as claimed in claim 4 further including a bubble detector cooperable with said photon counter to sense an air liquid interface in a tube that is disposed in said cylindrical passageway.

6. The apparatus as claimed in claim 1 wherein the light-receiving end of said fiber optic ribbons is in the form of a band of predetermined cross-sectional shape.

7. The apparatus as claimed in claim 6 wherein the cross-sectional shape of said band is a rectangle and said light-receiving end is rectangular.

8. The apparatus as claimed in claim 1, wherein said means for maintaining the radial arrangement of said fiber optic ribbons include a mounting core and said fiber optic ribbons are supported in said mounting core.

9. The apparatus as claimed in claim 8, wherein said mounting core includes a plurality of slots extending radially from said lateral axis and each of said slots correspond to respective said fiber optic ribbons such that each of said fiber optic ribbons is accommodated in a separate one of said slots.

10. The apparatus as claimed in claim 8, wherein said mounting core includes a plurality of segments arranged around said lateral axis, said segments being radially spaced such that the radial spacing accommodates said fiber optic ribbons.

11. The apparatus as claimed in claim 10, wherein said segments are formed as sectors of a cylinder.

12. The apparatus as claimed in claim 10, including a substantially light-proof housing for said segments, said housing having one opening in alignment with said cylindrical passageway, to permit accommodation of said tube into said housing for disposition in said cylindrical passageway.

13. The apparatus as claimed in claim 10, wherein said lightproof enclosure includes a substantially light-proof housing for said segments, said housing having one opening in alignment with said cylindrical passageway, to permit accommodation of said tube for extension into and out of said housing while being disposed in said cylindrical passageway.

14. An apparatus for collecting and transmitting chemiluminescent light comprising a) a plurality of fiber optic ribbons, each said fiber optic ribbon having one free end for receiving light and an opposite end for transmitting light, b) said light-receiving ends being located on the periphery of a substantially cylindrical path such that said light-receiving ends form the locus of the substantially cylindrical path, and c) means for collectively maintaining alignment of the light-receiving ends of said fiber optic ribbons at the periphery of the substantially cylindrical path in a light proof enclosure, such that said light-receiving ends are adapted to embrace a tube containing liquid with analyte undergoing chemical reaction, whereby chemiluminescent light emitted by said chemical reaction passes through the light-receiving ends of said fiber optic ribbons to said light-transmission ends.

15. The apparatus as claimed in claim 14 wherein said light-receiving end portions are uniformly distributed around said cylindrical path.

16. The apparatus as claimed in claim 14 wherein said light-receiving end portions are nonuniformly distributed around the periphery of said cylindrical passageway.

17. The apparatus as claimed in claim 14 including means for collecting together in the form of a cable the light-transmission ends of said fiber optic ribbons.

18. The apparatus as claimed in claim 14 wherein said means for maintaining alignment of the light-receiving ends include a core with positioning means for positioning the light-receiving ends.

19. The apparatus as claimed in claim 18 wherein a mirror is mounted to said core to receive light generated at the cylindrical passageway such that said mirror reflects light generated at said cylindrical passageway back to the cylindrical passageway for pickup by the light-receiving ends at the cylindrical passageway.

20. The apparatus as claimed in claim 18 wherein said cylindrical passageway includes a lateral axis and said positioning means includes a plurality of positioning sections that define slots extending radially from said lateral axis, each of said slots holding one of the light-receiving end portions of said fiber optic ribbons.

21. The apparatus as claimed in claim 20 wherein said core is mounted within a substantially light proof housing that constitutes said lightproof enclosure, said housing having opposite openings in alignment with said cylindrical passageway to accommodate said tube when said tube is disposed in said cylindrical passageway.

22. The apparatus as claimed in claim 20 wherein at least one of said positioning sections is removable from said core to provide radial access to said cylindrical passageway.

23. The apparatus as claimed in claim 20 wherein a portion of one of said positioning segments is removable from said core to provide radial access to said cylindrical passageway.

24. The apparatus as claimed in claim 20 wherein said positioning sections are arranged around said lateral axis and are radially spaced from each other such that the radial spacing accommodates said fiber optic ribbons.

25. The apparatus as claimed in claim 24 wherein said positioning sections are formed as sectors of a cylinder.

26. A method of collecting and transmitting chemiluminescent light comprising the steps of, a) arranging a plurality of fiber optic ribbons having opposite ends radially around a lateral axis such that one end portion of each of said fiber optic ribbons is in a lightproof enclosure, with the one end portions substantially equidistant from said lateral axis and defining a cylindrical passageway around the lateral axis, b) locating a fluid sample containing an analyte within the confines of the cylindrical passageway in alignment with the one end portion of each of the fiber optic ribbons, c) collecting any light established within the cylindrical passageway from the fluid sample through the one end portion of said fiber optic ribbons as light-receiving end portions, and d) transmitting light from the light-receiving ends of the fiber optic ribbons to the opposite end of the fiber optic ribbons and to a receiving station for conversion into selected data.

27. A method of selectively illuminating and collecting light from an analytical sample to quantify the analyte in the sample comprising the steps of, a) arranging a plurality of fiber optic ribbons having opposite ends radially around a lateral axis such that one end portion of each of said fiber optic ribbons is in a lightproof enclosure, with the one end portions substantially equidistant from said lateral axis and defining a cylindrical passageway around the lateral axis, b) locating a fluid sample containing an analyte within the confines of the cylindrical passageway in alignment with the one end portion of each of the fiber optic ribbons, c) sending an input light beam from the opposite end of at least one of the fiber optic ribbons to the cylindrical passageway to pass through the analyte, d) collecting light from the input beam in the cylindrical passageway after the light has passed through the analyte, such light collection being made at the one end of at least another of the fiber optic ribbons, and e) transmitting the collected light to the opposite end of the other fiber optic ribbon and to a receiving station for conversion into selected data.

28. The method of claim 27 wherein the input light beam is an exitation beam for producing fluorescent light at the cylindrical passageway.

29. The method of claim 27 wherein the input light beam is an incident beam for producing multi-angled light scattering at the cylindrical passageway.

30. The method of claim 27 wherein the input light beam has a predetermined light intensity and a portion of said input light beam is absorbed by the analyte depending upon the amount of the analyte present in the cylindrical passageway.

31. The method of claim 27 wherein the input light beam is an exitation beam for producing a first polarized light beam at the cylindrical passageway, and collecting a second polarized light from the cylindrical passageway after it has passed through the analyte.

32. The method of claim 27, including a) constituting the fiber optic ribbon of optic fibers, b) arranging the one end of the optic fibers in the fiber optic ribbons in an aligned configuration, and c) arranging the opposite end of the optic fibers in the fiber optic ribbons in a coherent arrangement in a cable such that the cable has a coherent end.

33. The method of claim 32, including placing a mask at the coherent end of the cable to define illumination and light-collecting portions of the cable.

* * * * *